United States Patent
Africk (10) Patent No.: US 7,844,405 B2
(45) Date of Patent: Nov. 30, 2010

(54) STATIC AND ULTRASONIC METHODS FOR MEASURING COMPRESSIBILITY AND DENSITY OF SMALL PARTICLES

(76) Inventor: Steven A. Africk, 30 Fenwick Rd., Newton, MA (US) 02468

( * ) Notice: Subject to any disclaimer, the term of this patent is extended or adjusted under 35 U.S.C. 154(b) by 83 days.

(21) Appl. No.: 11/990,472

(22) PCT Filed: Sep. 8, 2006

(86) PCT No.: PCT/US2006/034920

§ 371 (c)(1),
(2), (4) Date: Feb. 14, 2008

(87) PCT Pub. No.: WO2007/030655

PCT Pub. Date: Mar. 15, 2007

(65) Prior Publication Data

US 2009/0138216 A1    May 28, 2009

Related U.S. Application Data

(60) Provisional application No. 60/715,284, filed on Sep. 8, 2005.

(51) Int. Cl.
*G01F 19/00* (2006.01)
(52) U.S. Cl. .............................. 702/54; 702/11; 702/16; 702/189; 73/152.05; 73/866; 175/39; 175/40; 175/48; 324/303; 324/376

(58) Field of Classification Search .................... 702/11, 702/16, 54, 137–138, 189; 73/152.05, 866; 175/39, 40, 48; 324/303, 376
See application file for complete search history.

(56) References Cited

U.S. PATENT DOCUMENTS

| 4,688,238 A | 8/1987 | Sprunt et al. |
| 5,486,762 A * | 1/1996 | Freedman et al. ........... 324/303 |
| 6,968,274 B2 | 11/2005 | Tutuncu et al. |

OTHER PUBLICATIONS

Richardson et al., 'Dynamic Measurement of Sediment Grain Compressibility at Atomospheric Pressure Accoustic Applications', Jul. 2002, vol. 27, No. 3, IEEE Publication, pp. 593-601.*

* cited by examiner

*Primary Examiner*—Mohamed Charioui
*Assistant Examiner*—Elias Desta
(74) *Attorney, Agent, or Firm*—Weingarten, Schurgin, Gagnebin & Lebovici LLP (57) ABSTRACT

A method of measuring the compressibility, and/or the density, of small particles, and especially nano-particles, in suspension is described. The static method uses steady pressures and measures the d-c (static) compressibility of particles. The ultrasonic method utilizes an ultrasonic pulsed doppler system to measure the compressibility of particles at ultrasonic frequencies, which may differ from static values. These methods can also be used together to provide overlapping and complementary information about the particles. In addition, the ultrasonic pulsed doppler system also provides a way to measure particle density.

21 Claims, 5 Drawing Sheets

STATIC AND ULTRASONIC METHODS FOR MEASURING COMPRESSIBILITY AND DENSITY OF SMALL PARTICLES

CROSS REFERENCE TO RELATED APPLICATIONS

This application claims the priority of U.S. Provisional Application No. 60/715,284 filed Sep. 8, 2005 entitled, STATIC AND ULTRASONIC METHODS FOR THE MEASUREMENT OF COMPRESSIBILITY AND/OR DENSITY OF PARTICLES AND NANOPARTICLES IN SUSPENSION, the whole of which is hereby incorporated by reference herein.

STATEMENT REGARDING FEDERALLY SPONSORED RESEARCH OR DEVELOPMENT

N/A

BACKGROUND OF THE INVENTION

Measurement of particle compressibility can provide information about the mechanical properties and the structure of the particles that can be useful in many applications, including research and development and quality assurance for particle manufacturing and subsequent processing.

One application of compressibility measurement is the monitoring of modifications to particles as they are engineered for specific applications. In particular, the compressibility of small particles can change due to the addition of "cargo" or "payloads" to the particles. The incorporation of, for example, molecules, e.g., biomolecules, into the interior of micelles or emulsions or into the normally empty volumes of dendrimers will reduce the compressibility of these particles. Measurement of compressibility and changes in compressibility of the particles can be used to monitor the uptake of these molecules, providing a quality control process for the functionalization of small particles. In medicine, these measurements can monitor the uptake of diagnostic or therapeutic agents, e.g., into nanoparticles for delivery to cells either during particle manufacture or at the point of functionalization. This could include final steps that take place in the clinic immediately prior to the introduction of loaded particles to a patient. Release of cargo from particles can also be monitored.

BRIEF SUMMARY OF THE INVENTION

The invention is directed to measuring the compressibility, and/or the density, of small particles, and especially nanoparticles, in suspension. Two types of methods to measure the bulk compressibility of small particles are described. The static method uses steady pressures and measures the d-c (static) compressibility of particles. The ultrasonic method utilizes the Ultrasonic Pulsed Doppler (USPD) system described in U.S. patent application Ser. No. 11/272,032,[1] hereby incorporated by reference herein. In the ultrasonic method, the USPD system is used to measure the compressibility of particles at ultrasonic frequencies, which may differ from static values. These methods can also be used together to provide overlapping and complementary information about the particles. In addition, the USPD system also provides a way to measure particle density.

Thus, in one aspect, the method of the invention is directed to measuring the static bulk compressibility of particles including the steps of providing a fluid suspension that includes the particles to be tested in a compatible fluid medium; placing the fluid suspension in a pressure vessel; pressurizing the fluid suspension; measuring deflection of the surface of the fluid suspension as a function of the applied pressure; and determining the static bulk compressibility of the particles from the measured deflection. In one embodiment, the pressurizing step includes impressing a pressure sealed piston into the fluid suspension. Alternatively, a pressurized gas is introduced above the surface of the fluid suspension. The static method can further include repeating the first five method steps following a possible change in status of the particles; and comparing the determined compressibility of the particles following the possible change in status to the determined compressibility of the particles before the possible change in status.

In another aspect, the method of the invention is directed to measuring the dynamic bulk compressibility or density of particles including the steps of providing a fluid suspension that includes particles to be tested in a compatible fluid medium; generating, from a transducer, an interrogating ultrasonic signal consisting of tone bursts of one or more frequencies directed into the fluid suspension, wherein the fluid suspension is in motion or is caused to become in motion by the interrogating signal; measuring the ultrasonic scattered power from the interrogating signal; determining the proportionality factor m from the ratio of the scattered power to the concentration of the particles in the fluid medium; and computing the compressibility or density from the proportionality factor m. In one embodiment, in the computing step, m is equal to $K\,\Phi^2/r^2$, where r is a measure of the average distance between the measurement point and the scattering particles; K is a system calibration factor determined by the details of the measurement system; and $$\Phi = \frac{1}{3}k_0^2 a^3 \left[ \frac{\kappa_1 - \kappa_0}{\kappa_0} + \cos\theta \frac{3(\rho_1 - \rho_0)}{2\rho_1 + \rho_0} \right],$$

where $k_0$ is $2\pi f/c$ (where f is the interrogating frequency and c is the sound speed in the fluid medium); a is the particle radius; $\kappa_1$ and $\kappa_o$ are the compressibilities of the particles and the fluid medium, respectively, at the interrogating frequency; $\rho_1$ and $\rho_0$ are the densities of the particles and the fluid medium, respectively; $\Phi$ is the angular distribution factor (related to the scattering cross section by $\sigma=|\Phi|^2/\pi a^2$); C is the concentration of particles by volume; and $\theta$ is the angle at which the measurement is made. Preferably, the interrogating ultrasonic signal is generated from a transducer exposed to the fluid suspension, e.g., directly exposed or exposed to the fluid suspension through an ultrasonically transparent medium. The fluid suspension can be, e.g., contained within a vessel or it can be a flowing stream, for example, moving into or out of a batch processing system. In one embodiment, the ultrasonic scattered power measured is backscattered power, which is measured at the interrogating transducer.

Alternatively, the ultrasonic scattered power measured is both back and forward scattered power, the back scattered power being measured at the interrogating transducer and the forward scattered power being measured at a transducer 180° removed from the interrogating transducer; or the ultrasonic scattered power is measured at arbitrary angles. In another embodiment, the first three steps of the ultrasonic method are repeated one or more times at different concentrations of particles before the fourth step is carried out, and in the fourth step, the scattered power measured at each concentration of particles is plotted to form a concentration curve, m being determined as the slope of the concentration curve. For a one transducer system, the value of K is first determined experimentally by measuring the backscattered power using standard particles of known or estimated compressibility and density and calculating K according to the equation:

$$K = \frac{mr^2}{\left[\frac{\kappa_1 - \kappa_0}{\kappa_0} - \frac{3(\rho_1 - \rho_0)}{2\rho_1 + \rho_0}\right]^2 \left(\frac{1}{3}k_0^2 a^3\right)^2}$$

If the density of the particles is known, the compressibility of the particles is calculated according to the equation:

$$\frac{\kappa_1 - \kappa_0}{\kappa_0} = \frac{3(\rho_1 - \rho_0)}{2\rho_1 + \rho_0} + \frac{r\sqrt{\frac{m}{K}}}{\left(\frac{1}{3}k_0^2 a^3\right)}.$$

Alternatively, if it is known that the density term is very much smaller than the compressibility term, the compressibility of the particles is calculated according to the equation:

$$\frac{\kappa_1 - \kappa_0}{\kappa_0} = \frac{r\sqrt{\frac{m}{K}}}{\left(\frac{1}{3}k_0^2 a^3\right)}.$$

In another embodiment, the density contrast of the particles with the fluid medium is not known or, alternatively, is known not to be much smaller or larger than the compressibility contrast of the particles with the fluid medium, and the compressibility of the particles is determined according to the equation:

$$\frac{\kappa_1 - \kappa_0}{\kappa_0} = \frac{r_B}{\frac{2}{3}(k_0^2 a^3)}\sqrt{\frac{m_B}{K}} + \frac{r_F}{\frac{2}{3}(k_0^2 a^3)}\sqrt{\frac{m_F}{K}},$$

where $m_B$ and $m_F$ are separate proportionality factors for backscattered (B) and forward scattered (F) power, respectively, and $r_B$ and $r_F$ are the distances from the transducer (B) and transducer (F), respectively, to the focal zone. If, alternatively, the compressibility contrast of the particles with the fluid medium is not known or is known not to be much smaller or larger than the density contrast of the particles with the fluid medium, the density of the particles is determined according to the equation:

$$\frac{3(\rho_1 - \rho_0)}{2\rho_1 + \rho_0} = \frac{r_F}{\frac{2}{3}(k_0^2 a^3)}\sqrt{\frac{m_F}{K}} - \frac{r_B}{\frac{2}{3}(k_0^2 a^3)}\sqrt{\frac{m_B}{K}},$$

where $m_B$ and $m_F$ are separate proportionality factors for backscatter (B) and forward scattering (F), respectively, and $r_B$ and $r_F$ are the distances from the transducer (B) and transducer (F), respectively, to the focal zone.

In a further embodiment, the density contrast of the particles with the fluid medium is not known or, alternatively, is known not to be much smaller or larger than the compressibility contrast of the particles with the fluid, medium; the backscattered power is measured at the interrogating transducer; a second scattered power is measured at a transducer placed at an arbitrary angle θ removed from the interrogating transducer; and the compressibility of the particles is determined according to the equation:

$$\frac{\kappa_1 - \kappa_0}{\kappa_0} = \frac{3}{k_0^2 a^3 (1 + \cos\theta)}\left[r_\theta\sqrt{\frac{m_\theta}{K}} + \cos\theta r_B\sqrt{\frac{m_B}{K}}\right].$$

In a parallel manner, if the compressibility contrast of the particles with the fluid medium is not known or, alternatively, is known not to be much smaller or larger than the density contrast of the particles with the fluid medium, the backscattered power is measured at the interrogating transducer; the forward scattered power is measured at a transducer placed at an arbitrary angle θ removed from the interrogating transducer; and the density of the particles is determined according to the equation:

$$\frac{(\rho_1 - \rho_0)}{2\rho_1 + \rho_0} = \frac{1}{k_0^2 a^3 (1 + \cos\theta)}\left[r_\theta\sqrt{\frac{m_\theta}{K}} - r_B\sqrt{\frac{m_B}{K}}\right].$$

In another aspect, the invention is directed to a method for monitoring a change in particle size with pressure, the method including carrying out, in the order given, the steps of providing a fluid suspension comprising particles to be tested and a compatible fluid medium; placing the fluid suspension in a pressure vessel; pressurizing the fluid suspension at a first pressure; determining a value for particle size at the first pressure; repeating the third step at a second pressure; determining a value for particle size at the second pressure; and calculating any change in particle size with the change in pressure.

In a related aspect, the invention is directed to a method for monitoring a change in particle compressibility with pressure, the method including carrying out, in the order given, the steps of providing a fluid suspension comprising particles to be tested and a compatible fluid medium; placing the fluid suspension in a pressure vessel; pressurizing the fluid suspension at a first pressure; generating, from a transducer, an interrogating ultrasonic signal consisting of tone bursts of one or more frequencies directed into the fluid suspension, wherein the fluid suspension in the pressure vessel is in motion or is caused to become in motion by the interrogating signal; measuring the ultrasonic scattered power from the interrogating signal; determining a first proportionality factor m from the ratio of the scattered power to the concentration of the particles in the fluid medium; computing a first compressibility from the proportionality factor m; pressurizing the fluid suspension at a second pressure; generating, from a transducer, an interrogating ultrasonic signal consisting of tone bursts of one or more frequencies directed into the fluid suspension, wherein the fluid suspension in the pressure vessel is in motion or is caused to become in motion by the interrogating signal; measuring the ultrasonic scattered power from the interrogating signal; determining a second proportionality factor m from the ratio of the scattered power to the concentration of the particles in the fluid medium;

computing a second compressibility from the second proportionality factor m; and calculating any change in particle compressibility with the change in pressure.

In a further aspect, the invention is directed to a system for conducting both static and ultrasonic measurements of the compressibility of small particles, the system including a pressure vessel for pressurizing a fluid suspension of particles contained within the vessel; apparatus for applying pressure to a fluid suspension contained in the vessel; a stirring mechanism for generating particle motion in a fluid suspension of particles; a transducer for generating an ultrasonic signal exposed to the inside of the vessel, whereby, when a fluid suspension of particles is contained within the vessel, the transducer is exposed to the fluid suspension; and one or more transducers for receiving scattered ultrasonic energy from the particles in a fluid suspension contained within the vessel. In one embodiment, the transducer is directly exposable to the fluid suspension. Alternatively, the transducer is exposable to the fluid suspension through an ultrasonically transparent medium.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

The static method of measuring compressibility subjects a suspension of particles to a static pressure on the order of the compressibility of the particles. Two exemplary methods are described herein for applying a static pressure, using a piston and compressing a gas above the suspension of particles.

Figure 1:
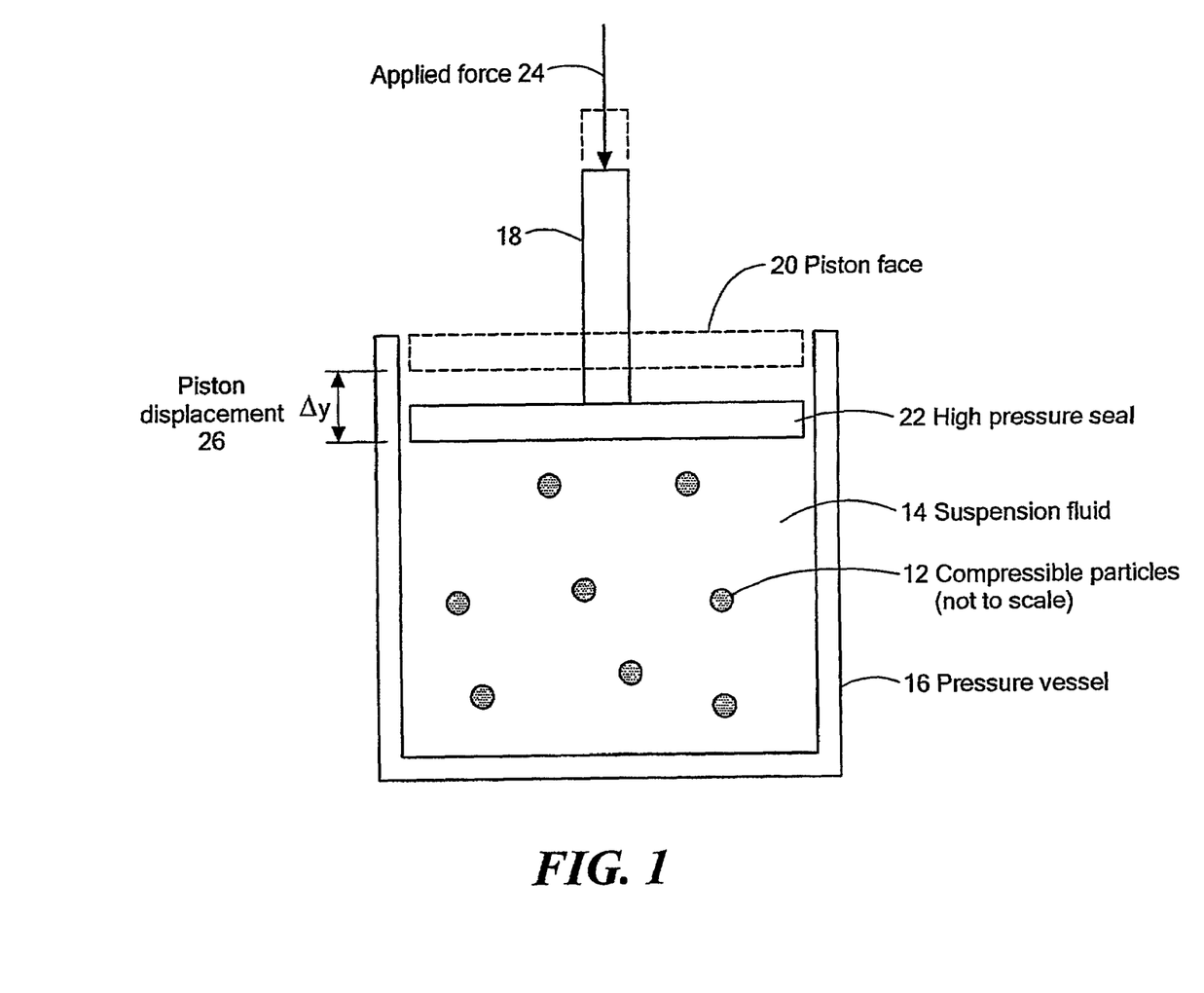
FIG. 1 is a schematic of a system for carrying out a static method of measuring compressibility according to the invention.

Referring to FIG. 1, in the first method, a monodisperse suspension of compressible particles 12 of static bulk modulus $B_P$ in suspension fluid 14 is placed in the pressure chamber of pressure vessel 16. A piston 18 having face area A 20 and rimmed by high pressure seal 22 is forced into suspension fluid 14 without leakage from the pressure vessel. Due to the force F imposed at the top 24 of piston 18, the piston moves into the fluid with displacement $\Delta y$ 26. This compresses the fluid suspension with a change in volume of $\Delta V = A \Delta y$. This volume change is related to the compressibilities of the fluid and the particles and to the initial volume of the fluid sample $V_0$ by $$\frac{\Delta V}{V_0} = \frac{A \Delta y}{V_0} = \left(\frac{1-C}{B_0} + \frac{C}{B_P}\right) P \qquad \text{Eq. (1)}$$

where:

C is the concentration of particles by volume, $B_0$ is the bulk modulus of the fluid (the reciprocal of the fluid compressibility $1/\kappa_0$);

$B_P$ is the bulk modulus of the particles (the reciprocal of particle compressibility $1/\kappa_1$); and P is the pressure generated within the sample.

Care must be taken to assure that there is no air or other gas in the volume between the fluid and the piston. Any air could be bled off by a vent in the piston; this could be augmented by a vacuum pump.

If the concentration C and the bulk modulus of the suspension fluid are known and $\Delta y$ is measured, particle bulk modulus $B_P$ and compressibility $\kappa_1 = 1/B_P$ can be calculated by Eq. (1).

Figure 2:
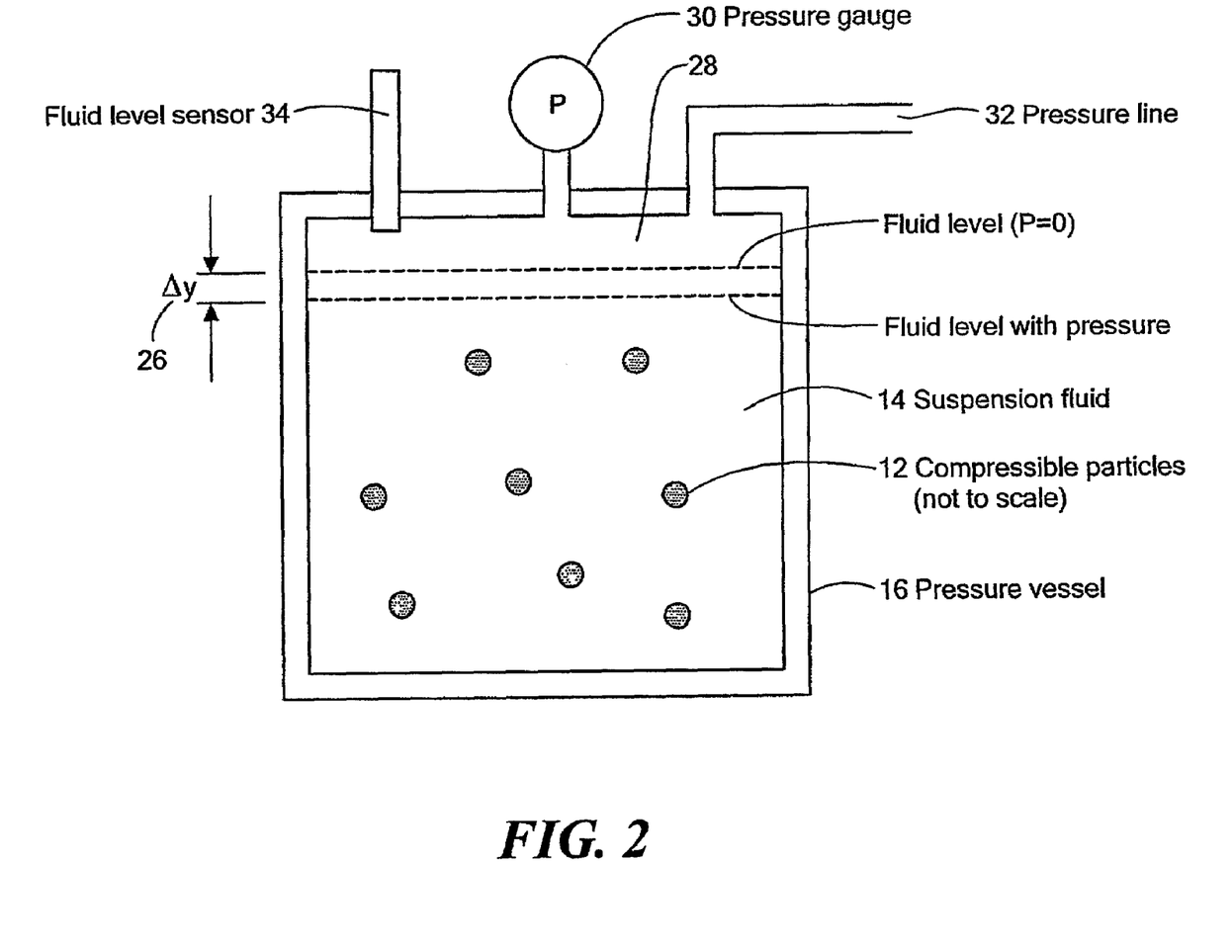
FIG. 2 is a schematic of an alternative system for carrying out a static method of measuring compressibility according to the invention.

In an alternative design, as shown in FIG. 2, instead of a piston, there is a volume of gas 28 above the fluid 14. The pressure in this gas is controlled by a compressor or a gas tank and monitored by pressure gauge 30. This pressure P is transmitted to the fluid through pressure line 32, and Eq. (1) again relates the deformation to the compressibility. In this configuration, the deflection $\Delta y$ 26 is that of the top surface of the fluid and $\Delta V = A \Delta y$, where A is the area of the fluid surface. This level deflection is monitored by one or more ultrasonic or optical probes in the top of the volume looking down at the fluid through a fluid level sensor 34.

The very simple algorithm in Eq. (1) is for a differential measurement in which it is assumed that the compressibility of the particles and the fluid do not vary with the pressure change. For small compressions, $\Delta V/V_0 \ll 1$, this will likely always be a good approximation. However, if the pressure generated in the sample becomes a substantial fraction of the bulk modulus of the particles, the particles will deform substantially, and depending on their structure, their compressibility will change with pressure. Uniform particle deformation (e.g., decrease in radius) will likely lead to a decrease in particle compressibility, while certain other types of shape changes such as buckling can lead to an increase in compressibility. In either case, the measured deformation may not be a linear function of the load such as is shown in the Eq. (1). In this case the governing equation to be solved is the more general:

$$\frac{dV}{V} = \left[\frac{1-C}{B_0} + \frac{C}{B_P(P)}\right] dP \qquad \text{Eq. (2)}$$

which can be integrated to yield:

$$\ln\frac{V_1}{V_0} = \int_0^P \left[\frac{1-C}{B_0} + \frac{C}{B_P(P)}\right] dP \qquad \text{Eq. (3)}$$

where $V_1$ is the volume at compression due to pressure P and $V_0$ is the original volume.

This equation can readily be integrated for any model for the change in bulk modulus with pressure, $B_p(P)$. For simple models for which there is only one parameter (e.g., Bp(P)=Bp ($P_0$)P/$P_0$ where $P_0$ is atmospheric pressure), this parameter can be expressed in terms of the known quantities and the volume V, and this parameter can be determined by the measured value of V with pressure. For more complicated models, additional measurements may be necessary.

The USPD technique is described in U.S. patent application Ser. No. 11/272,032,[1] hereby incorporated by reference herein. In this technique, acoustic scatter (primarily backscatter) at ultrasonic frequencies from a suspension of moving particles is measured. Typically, a backscattered power spectrum is generated by a fast Fourier transform of the signal backscattered from a series of tone bursts. Backscattered power is then summed at frequencies that differ from those associated with the interrogating signal. The differences in frequencies are generated by Doppler shifts due to particle motions. These motions can be due to bulk flow, e.g., in a stirred sample, or to other flows, such as that of particles entering or exiting a processing step, e.g., during particle manufacture. Flow away from the transducer can also be generated by the acoustic interrogating signal itself by acoustic Eckart streaming or other similar mechanism associated with the interrogation signal, giving rise to a force on the particles, which results in their motion.

Now, in the method of the invention, consider the scattered pressure $p_s(r)$ measured at a distance r from an interrogating transducer at the angle θ due to an interrogating plane wave $p_i(r)$ propagating in the forward direction (θ=0). The resulting scattered power π is proportional to the square of the scattered pressure $p_s^2(r)$ and also related to the properties of the particles (modeled as fluid spheres in the long wavelength limit, appropriate for particles smaller than 100 microns in the 10 Mhz range) via $$\Pi = \frac{K}{r^2}\Phi^2 C = mC \qquad \text{Eq. (4)}$$

where, as described in Coussis, (2002)[2], $$\Phi = \frac{rp_s(r)}{p_i(r)} = \frac{1}{3}k_0^2 a^3 \left[\frac{\kappa_1 - \kappa_0}{\kappa_0} + \cos\theta\frac{3(\rho_1 - \rho_0)}{2\rho_1 + \rho_0}\right] \qquad \text{Eq. (5)}$$

and $k_0$ is $2\pi f/c$, where c is the sound speed in the fluid medium and f is the interrogating signal frequency;

a is the particle radius;

$\kappa_1$ and $\kappa_0$ are the compressibilties of the particles and the fluid medium, respectively, at the signal frequency;

$\rho_1$ and $\rho_0$ are the densities of the particles and the fluid medium, respectively;

Φ is the angular distribution factor (related to the scattering cross section by $\sigma = |\Phi|^2/\pi a^2$);

C is the concentration of particles by volume;

K is a system calibration factor determined by the details of the measurement system, such as the stir rate, the incident pressure wave, etc.; and θ is the angle at which the measurement is made. For backscatter, cos θ=−1.

Thus, m is the proportionality factor π/C (or K $\Phi^2/r^2$). If measurements are made over a range of concentrations, m is the slope of the resulting concentration calibration curve.

The distance r is the separation between the measurement point and the scattering particle. The transducers used in a USPD system are highly focused, and there is a very small volume (smaller than 0.1 mm$^3$) located at the focus in which the pressure fields are very large. The scattered pressures can be assumed to originate only from within this focal zone through which the particles move, and the distance between its center and the measuring transducer is taken as the measure of r. For backscatter measured by the same transducer that generates the interrogating signal, this distance is essentially the focal length of the transducer. If additional transducers are used, their distance to the focal zone may not be the same (unless they are arranged around a ring with radius equal to the focal length).

This property of the USPD system allows it to be used in a test chamber of almost arbitrary size or shape. As long as the focal zone is within the fluid inside the chamber and there is a steady uniform flow of particles through the zone, measurements can be made, regardless of what happens elsewhere in the chamber. For single transducer operation, all that is needed is a single port or an acoustically (i.e., ultrasonically) transparent window through which the ultrasonic energy can propagate. If multiple transducers are required, the vessel shape must also allow for attachment of the additional transducers. Consequently, it is not difficult to incorporate USPD into existing facilities.

The terms in brackets in Eq. (5) represent the compressibility and density contrasts between the particle and the fluid medium. If there were no contrast, the action of the incident wave would not distinguish the particle from the medium and there would be no scattering. This scattering strength is proportional to the square of frequency (through $k_0^2$) and the cube of particle radius. The scattering due to the compressibility term is independent of the angle of measurement (i.e., it is omnidirectional) while that due to the density term has a cosine dependence (i.e., a dipole pattern). This formula describes scattering from a monodispersed suspension of particles of radius a. If there is a distribution of sizes, this term can be replaced by an appropriate mean value of the radius.

Figure 3:
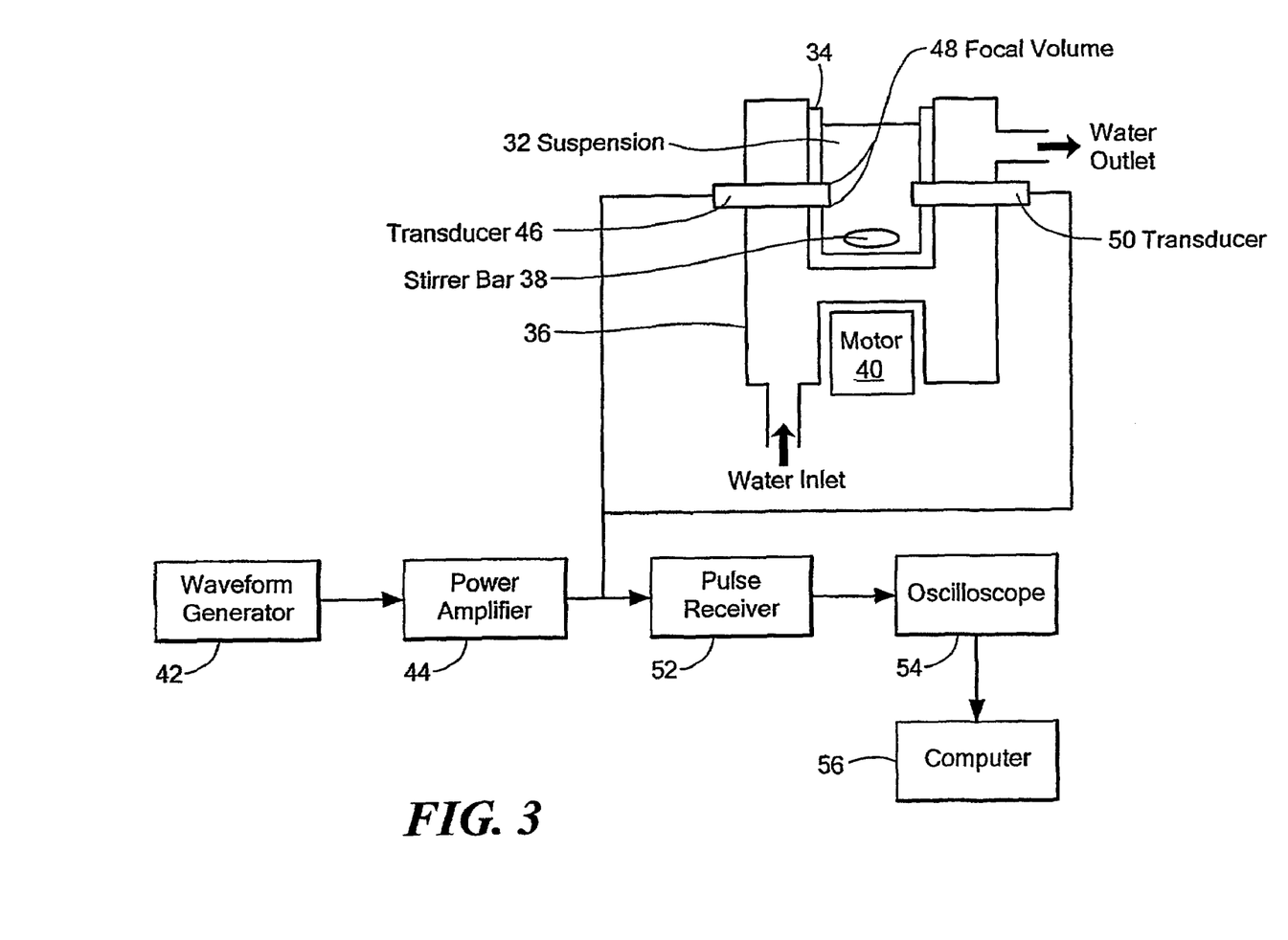
FIG. 3 is a schematic of a USPD system for measuring compressibility or density according to the invention.

In the simplest USPD configuration, only backscatter is measured. This measurement uses a single transducer both to launch the interrogating signals and to detect the backscattered signals. A schematic of an exemplary backscatter-based system is shown in FIG. 3. Multiple transducers can be required under certain circumstances. These can be placed at various positions inside the chamber walls. In many such applications, only two transducers are necessary, with the simplest arrangement being that the second transducer is placed opposite the interrogating transducer, from which position it measures the forward-scattered pressure.

Referring to FIG. 3, in a particular configuration, the particle suspension 32 is placed in a cylindrical chamber 34 surrounded by a water jacket 36 to maintain temperature. A stirrer bar 38 is at the center of the bottom of the chamber and is driven by an electric motor 40 mounted below it. A waveform generator 42 generates an interrogating signal consisting of a series of tone bursts at a center frequency (e.g., 16 Mhz) of finite widths (e.g., 30-50 cycles) with separation selected to insure that the scattered energy arrives at the measuring transducer(s) between the tone bursts (e.g., 7 μsec). If additional power is needed beyond that produced by the signal generator, a power amplifier 44 is used. The amplified interrogating signal is fed to a highly focused transducer 46. The interrogating signal propagates to the small focal zone 48 within the suspension where the strongest scattering by the particles of the ultrasonic signal takes place. The backscattered energy from the focal zone propagates back to the transducer. Other transducers 50 can be used to measure scattered energy at other than the backscatter direction. The combination of interrogating and backscattered signals, consisting of a series of large tone bursts between which the very low level Doppler shifted backscattered energy appears, is sent to the pulse/receiver 52. The pulse receiver performs two functions. It amplifies the signal (by, e.g., 39 dB) and it limits the output of the interrogating-signal portion of this signal to, e.g., 1.5-3 Vpp. This brings the backscattered signal energy to a sufficiently high level so that it can be digitized in an oscilloscope 54 while limiting the high values to levels that can also be fed to the oscilloscope without further modification.

The oscilloscope 54 is used to perform a fast Fourier transform (FFT) on segments of the incident signal of a length determined by the desired bin-width of the resulting power spectrum. For example, the FFT of a 40 msec long signal has a bin width of 25 Hz, which is of sufficient resolution for many USPD applications. A number of the resulting FFTs (e.g., 250) are collected in a computer 56 where they are averaged to form an average spectrum. These averaged spectra contain a large peak at the interrogating signal center frequency representing the interrogating signal and power in bins separated from this main peak associated with the Doppler-shifted scattered power from the particles. The total scattered power for each spectrum is determined by adding up the power in those bins representing scattered power from the moving particles. A number of these scattered power estimates are combined to form a measure of the total scattered power, e.g., backscatter, for a particular suspension.

In the method of the invention, several preferred methods for absolute measurement of the compressibility and/or the density of particles in suspension by USPD are contemplated. The method in general requires two steps, the first to estimate the quantity in brackets in Eq. (5), and the second to determine the compressibility and/or the density of the particles given the estimate of the term in brackets.

If the measurement system calibration constant K and the particle radius are known, or if by some other means the quantity $Ka^6$ is known, measurements of backscattered power ($\cos\theta=-1$) vs. concentration allow determination of the term in brackets that describes the physical characteristics of the particle (the compressibility and density contrasts) through solving Eqs. (4) and (5) to obtain:

$$\left[\frac{\kappa_1 - \kappa_0}{\kappa_0} - \frac{3(\rho_1 - \rho_0)}{2\rho_1 + \rho_0}\right] = \frac{\Phi}{\frac{1}{3}k_0^2 a^3} = \frac{r\sqrt{\frac{m}{K}}}{\left(\frac{1}{3}k_0^2 a^3\right)} = \frac{r\sqrt{\frac{m}{Ka^6}}}{\left(\frac{1}{3}k_0^2\right)} \quad \text{Eq. (6)}$$

The quantities m and K must be known to determine the term in brackets by the measurements described herein. The proportionality factor m, the ratio of backscattered power to concentration, is the primary measured quantity in this method. It is determined by Eq. (4) given the backscattered power for one or more concentrations of the particle in question. Measurements over a range of values of concentration can provide a concentration calibration curve showing the relationship between concentration and backscatter. The process of constructing this type of curve can often provide insights into the operation of the system. For example, the curve so constructed may have a non-zero y-intercept due to noise within the measurement system, the identification and elimination of which can provide better estimates of m.

The system calibration factor K is a function of the details of the measurement system, including the frequency, instrument sensitivities, gains, stirring rate, transducer characteristics, and so on. When more than one transducer is used or if there is more than one measurement position, a single value for K is possible when all the transducers are identical and use identical processing. (Otherwise, different values for K may need to be defined for different positions, which will introduce additional complexity into the interpretation of the data.)

The value of K can be determined experimentally for a specific measurement system through Eqs. (4)-(6), making use of a particle for which the term in brackets is known. Ideally, a particle of known compressibility and density could serve as a standard. In this case, the term in brackets could be calculated and measurements of backscattered power alone can be used to determine K by Eq. (6). However, there is limited knowledge of particle compressibility at ultrasonic frequencies, and only a few such standards are available at this time.

Alternatively, the system calibration constant K can be determined by measuring quantities that are a function only of scattering from the density terms, as this property of particles is generally known. For example, if it can be determined that the density contrast term in brackets is significantly larger than the compressibility term (e.g., for rigid and heavy particles), then the term in brackets can be estimated by the density term alone, and the constant K can be determined directly through Eqs. (4)-96) using backscattered-power measurements.

If the compressibility term cannot be ignored a priori, the value of K can be measured by combining measurements of backscattered and forward scattered energies. Separate proportionality factors for backscatter (B) and forward scattering (F) are measured so that $$\pi_B = m_B C = K[\Phi(\theta=\pi)]^2 C/r_B^2 = K\Phi_B^2 C/r_B^2$$

$$\pi_F = m_F C = K[\Phi(\theta=0)]^2 C/r_F^2 = K\Phi_F^2 C/r_F^2 \quad \text{Eq. (7)}$$

where $r_B$ and $r_F$ are the distances from the transducers to the focal zone.

Combining Eqs. (5) and (7) and forming the difference between the forward and backscatter terms produces:

$$\Phi_F - \Phi_B = r_F\sqrt{\frac{m_F}{K}} - r_B\sqrt{\frac{m_B}{K}} = \frac{2(\rho_1 - \rho_0)}{2\rho_1 + \rho_0}(k_0^2 a^3) \quad \text{Eq. (8)}$$

By Eq. (8), K can be determined from the measured values of $m_F$ and $m_B$ and the known density of the particle being measured. Solving for K yields:

$$K = \frac{r_F^2 m_F + r_B^2 m_B - 2r_F r_B \sqrt{m_F m_B}}{4k_0^4 a^6\left[\frac{\rho_1 - \rho_0}{2\rho_1 + \rho_0}\right]^2} \quad \text{Eq. (9)}$$

For a measurement made at an arbitrary angle, the equivalent expressions are:

$$\Phi_\theta - \Phi_B = r_\theta\sqrt{\frac{m_\theta}{K}} - r_B\sqrt{\frac{m_B}{K}} \quad \text{Eq. (10)}$$

$$= (1 + \cos\theta)\frac{(\rho_1 - \rho_0)}{2\rho_1 + \rho_0}(k_0^2 a^3)$$

and

-continued $$K = \frac{r_\theta^2 m_\theta + r_B^2 m_B - 2r_\theta r_B \sqrt{m_\theta m_B}}{k_0^4 a^6 (1 + \cos\theta)^2 \left[\frac{\rho_1 - \rho_0}{2\rho_1 + \rho_0}\right]^2} \quad \text{Eq. (11)}$$

where $r_\theta$ is the distance from the scattering particles to the measurement point at angle $\theta$.

Once K is known and m is measured, the term in brackets is computed via Eq. (6). The final step is determination of the compressibility and/or density from the term in brackets. Often the compressibility term is much larger than the density term. In this case, a backscatter measurement of the bracketed term alone gives a good approximation to the compressibility contrast, and since the compressibility of the fluid is presumed known, the compressibility of the particles can be determined in this manner.

If it is not known a priori that the density term is the smaller so that the bracketed term is a good measure of compressibility alone, additional measurements are required to solve for the two terms in brackets in order to determine the compressibility (or the density). Scattering measurements made over a range of angles θ can determine the shape of the angular distribution factor $\Phi$. This requires the use of multiple transducers and/or multiple measurement positions. If $\Phi$ is found to be omnidirectional, it can be concluded that the density term is small and the bracketed term can be approximated by the compression term alone. If not, the observed angular distribution can be considered to be a linear combination of omnidirectional and a dipole terms, and the detailed shape of the pattern can be fit to estimate the relative sizes of the two terms in the brackets. Often, measurements at only two positions (e.g., backscatter and forward scatter) suffice to simultaneously determine the compressibility and density.

Multiple measurements can also be made with fluids of differing density (but with the same compressibility). The relative importance of the density term will vary with the fluid density, and it will vanish when the density of the fluid matches that of the particles.

Once the magnitude of the density term is determined for a particular type of particle measurement, compressibility can be inferred from a measurement of the bracketed term without repeated estimation of the density term. In that case, the multiple-transducer measurements will not need to be repeated, and simple backscatter using only a single transducer can be implemented.

In the simplest implementation, if the measurements are sufficiently precise, it is possible to determine compressibility contrast with only two angles, by combining measurements of the forward-scattered and backscattered power. Since the contribution to the bracketed expression of the density term will be equal in magnitude and opposite in sign at these two angles (cos θ=1 and −1, respectively) the sum of the bracketed expression measured at these two angles will be equal to exactly twice the compressibility term, and the compressibility contrast will be proportional to this sum:

$$2\frac{\kappa_1 - \kappa_0}{\kappa_0} = \left[\frac{\kappa_1 - \kappa_0}{\kappa_0} + \frac{3(\rho_1 - \rho_0)}{2\rho_1 - \rho_0}\right] + \left[\frac{\kappa_1 - \kappa_0}{\kappa_0} - \frac{3(\rho_1 - \rho_0)}{2\rho_1 + \rho_0}\right] \quad \text{Eq. (12)}$$

Compressibility can be calculated by:

$$\frac{\kappa_1 - \kappa_0}{\kappa_1} = \frac{1}{\frac{2}{3}k_0^2 a^3}[\Phi(\theta = 0) + \Phi(\theta = \pi)] \quad \text{Eq. (13)}$$

$$= \frac{r_B}{\frac{2}{3}(k_0^2 a^3)}\sqrt{\frac{m_B}{K}} + \frac{r_F}{\frac{2}{3}(k_0^2 a^3)}\sqrt{\frac{m_F}{K}}$$

Similarly, the density of particles can be measured by forming the difference between the scattering functions:

$$\frac{3(\rho_1 - \rho_0)}{2\rho_1 + \rho_0} = \frac{1}{\frac{2}{3}k_0^2 a^3}[\Phi(\theta = 0) - \Phi(\theta = \pi)] \quad \text{Eq. (14)}$$

$$= \frac{r_F}{\frac{2}{3}(k_0^2 a^3)}\sqrt{\frac{m_F}{K}} - \frac{r_B}{\frac{2}{3}(k_0^2 a^3)}\sqrt{\frac{m_B}{K}}$$

As USPD can also measure particle size, simultaneous measurements of size and compressibility can be made.

Figure 4:
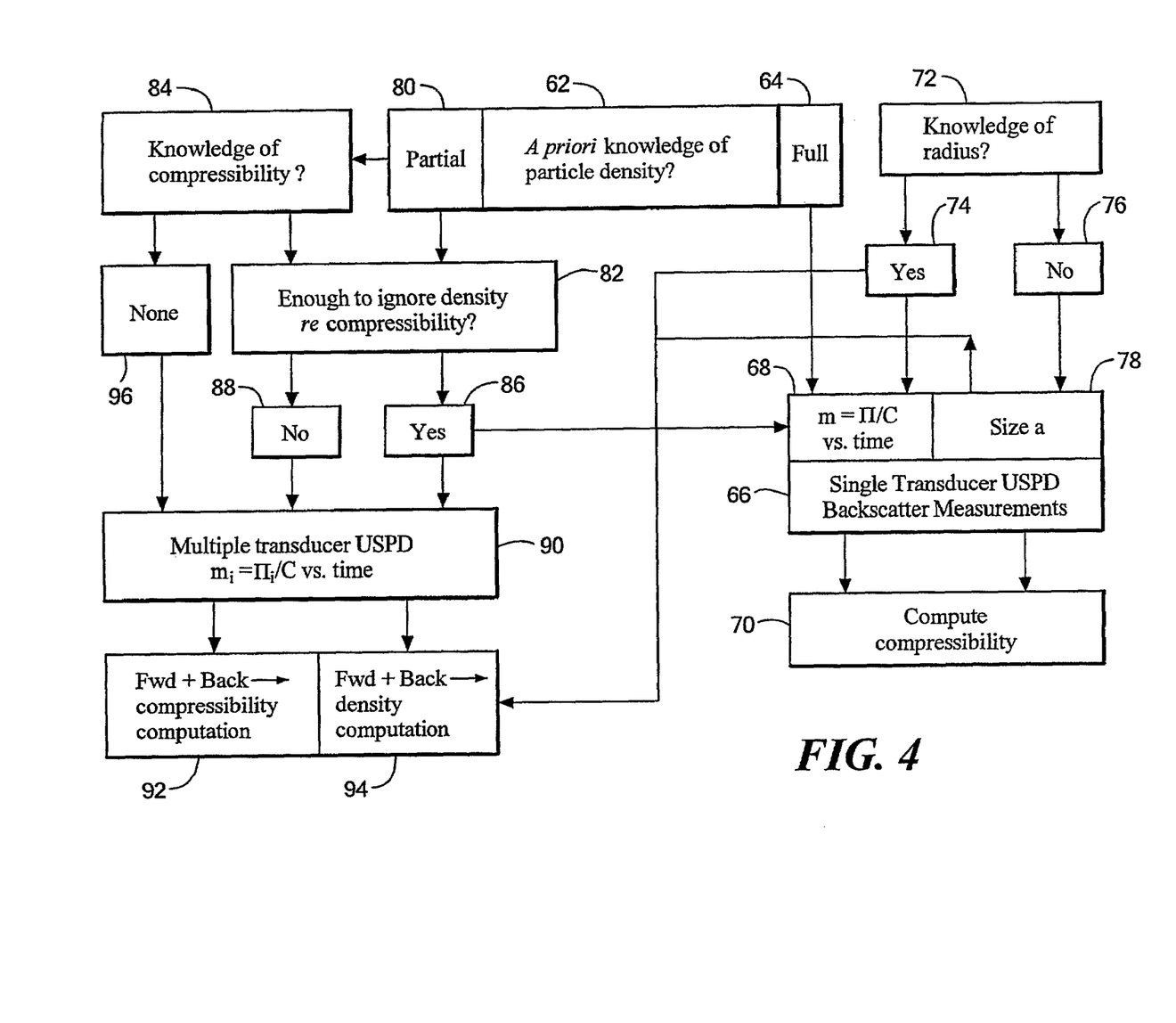
FIG. 4 is a flow chart showing choice of a USPD system according to the invention for measuring compressibility or density given a priori knowledge of certain particle properties.

A flowchart of the requirements for simple single-transducer backscatter measurements or measurements made with multiple transducers to determine compressibility depending on a priori knowledge of particle properties is presented in FIG. 4. A convenient place to begin practicing this method is by an assessment of the a priori knowledge of the density of the particle to be measured 62. If the density is known in full 64, determination of the term in brackets in Eq. (6) by a single-transducer 66 backscatter measurement of proportionality factor m 68 is sufficient to determine the compressibility 70, as long as the radius 72 of the particle is known 74. Typically, the radius is known a priori either by manufacturer's specification or other laboratory measurements (e.g., SEM, dynamic light scattering). If the radius is not known 76, USPD sizing 78 by single-transducer backscatter measurements 66 can be made with the same physical configuration used for the backscatter concentration measurements, except without stirring the fluid.

If there is only partial knowledge of the density 80, what is known must be compared 82 to what is known a priori about the compressibility 84. If there is adequate information to conclude that the density contrast is very much smaller than the compressibility contrast 86 (e.g., when the particles such as ultrasound contrast agents are known to have very high compressibility or when the particle density is quite close to that of water), single transducer backscatter measurements of proportionality factor m 68 can then be made. If not 88, multiple transducer measurements 90 of proportionality factors $m_i$ corresponding to the i-th transducer or transducer position are required. If, for example, both forward and backscattered power are measured, the sum 92 of the bracketed terms determines the compressibility while the difference 94 provides a measure of the particle density(s). (Use of more than two transducers or choices of other positions requires modification of the algorithms in boxes 92 and 94.) As with single-transducer measurements, the particle radius must be known to make these measurements. If the particle radius is not known a priori 96, USPD sizing 78 by single-transducer backscatter measurements can be made as before to determine a radius value for the analysis. This is always possible, as the multiple transducer USPD system can always be operated in the single-transducer mode used for sizing measurements.

Figure 5:
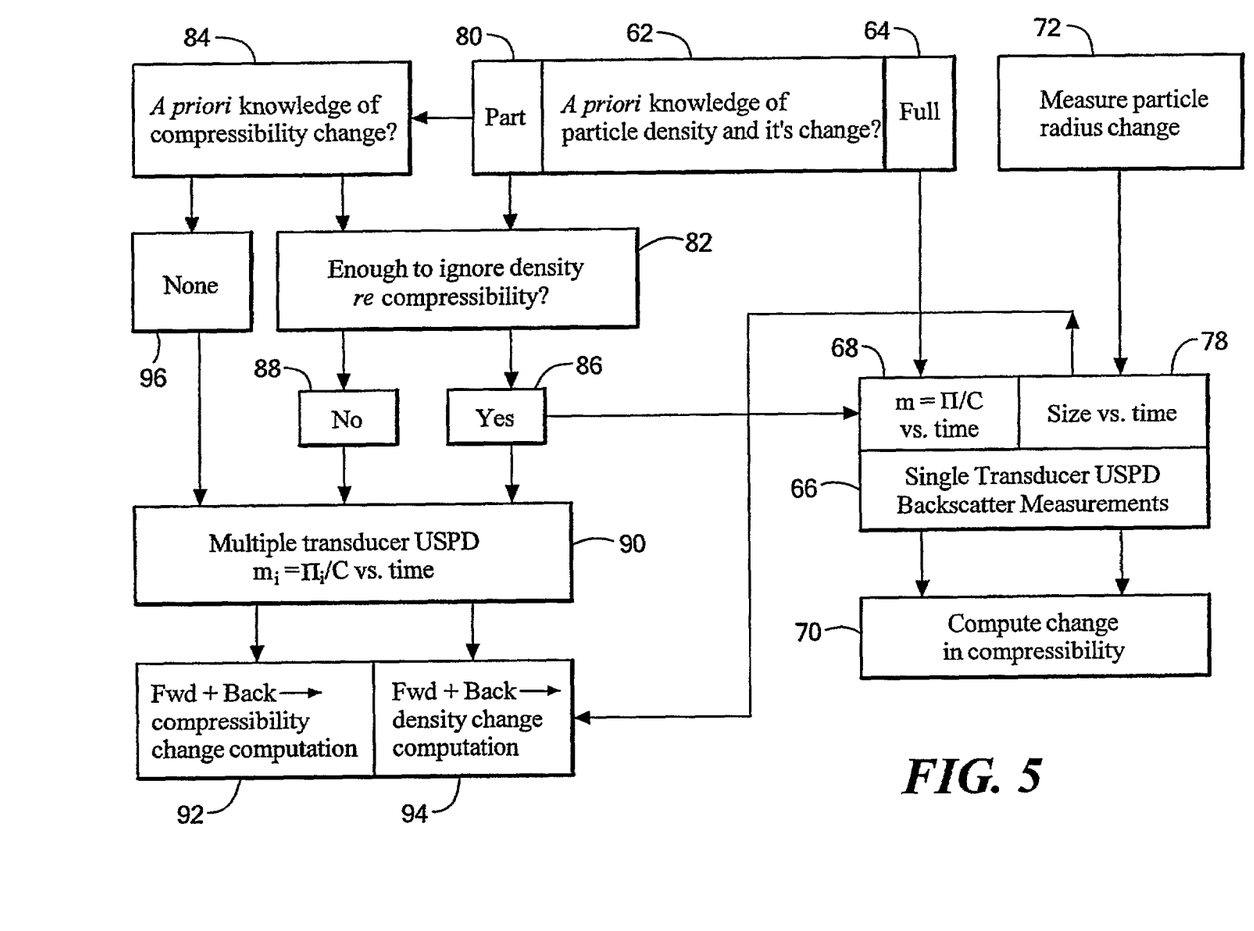
FIG. 5 is a flow chart showing choice of a USPD system according to the invention for measuring changes in compressibility or density given a priori knowledge of certain particle properties.

Changes in particle compressibility can be measured by observing changes in absolute measurements of compressibility with the methods described above, recognizing that the particle radius 72 can change with any process likely to lead to a change in compressibility. Referring to FIG. 5, unless there is reason to believe that the particle radius will not change, it is monitored by the USDP sizing method 78 at least before and after, and potentially during, any process being monitored for compressibility changes. Values for radius changes are required to compute compressibility changes, whether made with backscatter alone 66 or by multiple transducer methods 90.

Determination of the type of measurement required for differential compressibility begins with the a priori state of knowledge of the particle density 62. If this quantity is known 64, measurements of proportionality factor m vs. time 68 can be made with a single-transducer backscatter method 66, which, along with the value of radius vs. time 78, allows computation of compressibility changes with time 70. If, on the other hand, there is only partial knowledge of the behavior of particle density during the process 80, this information must be compared what is known a priori about the change in particle compressibility. If it can be concluded 82 that the changes in density can be ignored 86, only single transducer backscatter measurements 68 are made. On the other hand, if this cannot be safely concluded 88 or if there is no a priori information about compressibility changes 96, then multiple-transducer USPD measurements of proportionality constants $m_i$ are made 90. The simplest measurement of this type uses a second transducer opposite the first so that values of m for backscatter $m_B$ and forward scattering $m_F$ are used to compute the compressibility 92 and density 94 changes.

Changes in compressibility can also be inferred from changes in backscatter even when there is only partial knowledge of the particle's properties. In this case, the estimation of the change in compressibility begins with the usual knowledge of the proportionality factor m for a given particle type and measurement system in the form, $$\pi = mC. \qquad \text{Eq. (15)}$$

As described above, m can be determined on the basis of a single measurement, or as the slope of a concentration calibration curve based on multiple measurements made over a range of concentrations. If the particle suspension is changed by changes in particle compressibility and/or density (due to, for example, the uptake or release of molecular cargo), the value of m will change. By Eq. (6), the change in m will be related to the change in the bracketed term by:

$$\frac{\Delta\left[\frac{\kappa_1 - \kappa_0}{\kappa_0} - \frac{3(\rho_1 - \rho_0)}{2\rho_1 + \rho_0}\right]}{\frac{\kappa_1 - \kappa_0}{\kappa_0} - \frac{3(\rho_1 - \rho_0)}{2\rho_1 + \rho_0}} = \frac{1}{2}\frac{\Delta m}{m} - 3\frac{\Delta a}{a} \qquad \text{Eq. (16)}$$

or equivalently, $$\frac{\Delta\kappa_1}{\kappa_0} - 9\frac{\rho_0 \Delta\rho_1}{(2\rho_1 + \rho_0)^2} = \frac{r}{\frac{1}{3}k_0^2 a^3}\sqrt{\frac{m}{K}}\left(\frac{1}{2}\frac{\Delta m}{m} - 3\frac{\Delta a}{a}\right) \qquad \text{Eq. (17)}$$

where $\Delta\kappa_1$, $\Delta\rho_1$, $\Delta a$ and $\Delta m$ are the corresponding changes in particle compressibility, density, radius, and proportionality factor m.

These expressions relate changes in particle compressibility, density and radius with the change in the measured value of the proportionality factor m. The sizes of the changes in these parameters will depend on the experiment performed. For example, under pressurization, all three particle properties may change and changes in density and radius will likely be inversely related by:

$$\frac{\Delta\rho_1}{\rho_1} = -3\frac{\Delta a}{a} \qquad \text{(18)}$$

so that Eq. (17) becomes:

$$\frac{\Delta\kappa_1}{\kappa_0} - \left(\frac{9\rho_0\rho_1}{(2\rho_1 + \rho_0)} + \frac{r}{\frac{1}{3}k_0^2 a^3}\sqrt{\frac{m}{K}}\right)\frac{\Delta\rho_1}{\rho_1} = \frac{r}{\frac{2}{3}k_0^2 a^3}\sqrt{\frac{1}{Km}}\Delta m \qquad \text{Eq. (19)}$$

On the other hand, during the pick up or release of a cargo molecule, radius and density are less likely to change than compressibility. Here, if the size of the particle remains the same, the change in the density will be due to the mass of the cargo particle itself. If this is small with respect to the mass of the particle, the density change will also be small.

Returning to the more general case of Eq. (17) in which the particle radius and density are not directly related, if the density terms can be neglected, this reduces to the simple form:

$$\frac{\Delta\left[\frac{\kappa_1 - \kappa_0}{\kappa_0}\right]}{\frac{\kappa_1 - \kappa_0}{\kappa_0}} = \frac{\Delta\kappa_1}{\kappa_1 - \kappa_0} = \frac{1}{2}\frac{\Delta m}{m} - 3\frac{\Delta a}{a} \qquad \text{Eq. (20)}$$

or the equivalent:

$$\frac{\Delta\kappa_1}{\kappa_0} = \frac{r}{\frac{1}{3}k_0^2 a^3}\sqrt{\frac{m}{K}}\left(\frac{1}{2}\frac{\Delta m}{m} - 3\frac{\Delta a}{a}\right) \qquad \text{Eq. (21)}$$

and if a change in the radius is insignificant, this reduces to:

$$\frac{\Delta\kappa_1}{\kappa_0} = \frac{r}{\frac{2}{3}k_0^2 a^3}\sqrt{\frac{1}{mK}}\Delta m \qquad \text{Eq. (22)}$$

from which the change in particle compressibility can be simply calculated given the measured change in the value of m. This change in m can be determined by a measurement at a single point or over several such points with different concentrations.

Eq. (20) shows that in this approximation increasing compressibility of particles initially more compressible than the suspension fluid (expected for most nanoparticles) increases the proportionality factor m (or calibration curve slope) as long as the particle radius does not decrease significantly. If the particle starts out more compressible than the fluid ($\kappa_1 > \kappa_0$) the denominator in Eq. (20) is positive. Any decrease in particle compressibility ($\Delta\kappa_1 < 0$) will give rise to a decrease in m ($\Delta m < 0$).

This type of measurement can be used to monitor a process in which, for example, molecular cargo is added to a particle when the addition of molecules changes the compressibility of the host particles. Consider a process which begins with a suspension of host particles into which, for example, a molecular cargo species is added. A process in which the molecules become incorporated into the host particles then occurs. Assume also that particle density and radius do not vary significantly so that Eq. (22) holds and that the particles begin the process more compressible than the suspension fluid ($\kappa_1>\kappa_0$).

Before the addition of the molecules, the particle suspension will be characterized by its concentration C and a measured backscattered power $\pi$. Their ratio gives the initial value for m. When the cargo is added and the particle compressibility decreases, the measured backscatter $\pi$ will be reduced by $\Delta\pi$, leading to a change $\Delta m=\Delta\pi/C$, so that $\Delta m/m=\Delta\pi/\pi<0$. The measured change in compressibility $\Delta\kappa_1$ is then:

$$\Delta\kappa_1 = \frac{\Delta m}{2m}(\kappa_1-\kappa_0) = \frac{\Delta\Pi}{2\Pi}(\kappa_1-\kappa_0) \quad \text{Eq. (23)}$$

If the molecular uptake (or release) of cargo takes place on a time scale longer than that required to take enough data to form backscatter spectra, these changes can be tracked in real time.

Use

The methods of the invention, particularly the USPD technique, are useful in a wide variety of situations and circumstances, limited only by the imagination of the user. For example, an interrogating ultrasonic probe (transducer) can be incorporated within a dedicated test chamber in which batches of particles are subjected to quality assurance analysis. In another example, a transducer for use in practicing the method can be placed within (or, e.g., adjacent to an ultrasonically transparent window in) a processing unit in which a process of manufacture is taking place to monitor what is happening in the process in real time. Exemplary processing units include bioreactors or vessels in which, e.g., a sonication process is taking place to break particles down to smaller size, etc. An interrogating ultrasonic transducer can also be placed, e.g., in a flowing stream of particles coming out of (or going into) a processing step, or both, to measure the change during the step.

The type of measurement required to characterize changes in particles, or nanoparticles, will depend on whether certain changes can be ruled out based on theory or past experience. The most general approach must account for all effects.

For example, USPD can be used to measure the radius of particles directly. In the absence of stirring, the particles are accelerated to a velocity that is a function of their size by a process very similar to Eckart acoustic streaming. Backscatter spectra taken with a single transducer contain sharp peaks at frequencies well separated from the main interrogating signal. The frequencies of these peaks are determined by the Doppler shift due to particle motion away from the transducer. This motion is directly related to particle size which is measured in this manner. Changes in particle size can also be directly observed in changes in peak frequencies. Size measurements can be made before, during and after any intervention with the particles and the change in radius can be determined. This term is retained along with the change in the proportionality constant m on the right hand side of Eqs. (16) and (17) to indicate that these are both measured quantities, albeit by different aspects of the USPD technique.

Joint measurement of density and compressibility, and of changes in these quantities brought about by a change in particle status, can also be carried out. Changes in m and radius measured by USPD backscatter concentration and sizing methods with a single transducer determine the change in the term in brackets by Eqs. (16) and equivalently Eq. (17). This term is a function of change in compressibility and change in density. If it is known that the change in density can be ignored, the change in compressibility can be calculated with Eq. (21) or by comparison of measurements made before and after a change in status. Likewise, if it is known that the change in density is much larger than the change in compressibility, this change can be determined by ignoring the compressibility term in Eq. (17).

If the density change cannot be assumed to be insignificant, measurements with more than one transducer are necessary to solve for the two terms. In analogy to the two-transducer method used for absolute compressibility measurements an additional transducer is added opposite the interrogating transducer to measure the forward-scattered signal. (This transducer could be placed at one or more arbitrary angles as was explicitly shown in Eqs. (10) and (11)). When the second transducer is located at 180° from the interrogating transducer, the compressibility term is again isolated by the summation of the forward and backscattered signals:

$$2\frac{\Delta\kappa_1}{\kappa_0} = \frac{r_B}{\frac{1}{3}k_0^2a^3}\sqrt{\frac{m_B}{K}}\left(\frac{1}{2}\frac{\Delta m_B}{m_B}-3\frac{\Delta a}{a}\right)+ \frac{r_F}{\frac{1}{3}k_0^2a^3}\sqrt{\frac{m_F}{K}}\left(\frac{1}{2}\frac{\Delta m_F}{m_F}-3\frac{\Delta a}{a}\right) \quad \text{Eq. (24)}$$

with which the change in compressibility can be computed. Likewise, subtraction of these terms provides an independent measurement of the density change via:

$$18\frac{\rho_0\Delta\rho_1}{(2\rho_1+\rho_0)} = \frac{r_F}{\frac{1}{3}(k_0^2a^3)}\sqrt{\frac{m_F}{K}}\left(\frac{1}{2}\frac{\Delta m_F}{m_F}-3\frac{\Delta a}{a}\right)- \frac{r_B}{\frac{1}{3}(k_0^2a^3)}\sqrt{\frac{m_B}{K}}\left(\frac{1}{2}\frac{\Delta m_B}{mB}-3\frac{\Delta a}{a}\right) \quad \text{Eq. (25)}$$

The static and USPD measurement techniques can readily be combined into a single instrument in which a USPD transducer is incorporated into a pressure vessel used for static measurements. This configuration can allow direct comparisons between simultaneous measurements of the static and high-frequency compressibilties. As the USPD method can also provide particle size information, it will be possible to monitor particle size changes due to static pressure and to relate these changes to variations in compressibility. These results can generate insights into the relationships among particle size, shape and compressibility.

Combined measurements will also provide improved means to measure particle compressibility and density simultaneously. Static measurements can provide an independent measure of particle compressibility, which can then be used to provide a better estimate of density contrast in the dynamic measurements. This will be possible only insofar as the static and dynamic compressibilities are the same.

Compressibility changes brought about by, e.g., uptake of molecules or other cargo in particles or nanoparticles can also be monitored by the static methods described above and/or slight variations of these methods. The compressibility can be monitored during a process by successive cycles of adding a static force or pressure, measuring, e.g., the deflection of the piston or fluid surface, and releasing force or pressure before starting another measurement cycle. It may also be possible to subject the system to an initial force or pressure and then observe changes in the deflections or pressure as the cargo is taken up by the particles. If the compressibility is increased by the process and the particle radius does not change, the measured surface deformations would also increase with the process. On the other hand, if compressibility decreases, there would be no change in the system.

Alternatively, the applied static force or pressure can be cycled during a process during which the compressibility changes. Here, the response would differ from that which would be observed if the particle compressibility were constant. In the latter case, the response vs. time would, for small deformations, follow the cycled pressure. With changing compressibility, response vs. time would deviate from this behavior. If compressibility increased while the pressure or force were cycled, the deformation of the surface with increasing pressure would be larger than the decrease in the recovery period during which pressure is released. The rate of change of the level deflection can be calculated by taking the time derivative of Eq. (1), $$\frac{d}{dt}\frac{\Delta V}{V_0} = \left(\frac{1-C}{B_0} + \frac{C}{B_P}\right)\frac{dP}{dt} - \frac{PC}{B_P^2}\frac{dB_P}{dt} \qquad \text{Eq. (26)}$$

If the compressibility $B_P$ is initially known and the system is subjected to a varying pressure, the rate of change of $B_P$ can be calculated in terms of the measured time variation of the deflection by Eq. (10). Pressure variations of several kinds including linear increase or decrease, step functions (up or down) and cycling can be used.

REFERENCES

1. U.S. patent application Ser. No. 11/272,032 "Ultrasonic Method for Measuring Concentrations of Particles, Cells and Islets in Suspension," filed Nov. 14, 2005.
2. Coussis, Constantin-C (2002), "The significance of shape and orientation in single-particle weak-scatterer models," *J. Acoust. Soc. Am.*, 112 (3) Pt. 1.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method to measure the dynamic bulk compressibility or density of small particles comprising the steps of:
    (1) providing a fluid suspension comprising small particles to be tested and a compatible fluid medium;
    (2) generating, from a transducer, an interrogating ultrasonic signal consisting of tone bursts of one or more frequencies directed into the fluid suspension, wherein the fluid suspension is in motion or is caused to become in motion by the interrogating signal;
    (3) measuring the ultrasonic scattered power from the interrogating signal;
    (4) determining the proportionality factor m from the ratio of the scattered power to the concentration of the particles in the fluid medium; and
    (5) computing the compressibility or density from the proportionality factor m.

2. The method of claim 1, wherein, in the computing step, m is equal to $K\,\Phi^2/r^2$, where
    (1) r is a measure of the average distance between the measurement point and the scattering particles;
    (2) K is a system calibration factor determined by the details of the measurement system; and $$\Phi = \frac{1}{3}k_0^2 a^3 \left[\frac{\kappa_1 - \kappa_0}{\kappa_0} + \cos\theta \frac{3(\rho_1 - \rho_0)}{2\rho_1 + \rho_0}\right], \qquad (3)$$

where:
  $k_0$ is $2\pi f/c$, where f is the interrogating frequency and c is the sound speed in the fluid medium;
  a is the particle radius;
  $\kappa_1$ and $\kappa_0$ are the compressibilities of the particles and the fluid medium, respectively, at the acoustic frequency;
  $\rho_1$ and $\rho_0$ are the densities of the particles and the fluid medium, respectively;
  $\Phi$ is the angular distribution factor (related to the scattering cross section by $\sigma=|\Phi|^2/\pi a^2$);
  C is the concentration of particles by volume; and
  $\theta$ is the angle at which the measurement is made.

3. The method of claim 1, wherein, in step 2, the interrogating ultrasonic signal is generated from a transducer exposed to the fluid suspension.

4. The method of claim 3, wherein the transducer is directly exposed to the fluid suspension.

5. The method of claim 3, wherein the transducer is exposed to the fluid suspension through an ultrasonically transparent medium.

6. The method of claim 1, wherein the fluid suspension is a flowing stream.

7. The method of claim 1, wherein, in step 3, the ultrasonic scattered power measured is backscattered power, which is measured at the interrogating transducer.

8. The method of claim 1, wherein, in step 3, the ultrasonic scattered power measured is both back and forward scattered power, and wherein the back scattered power is measured at the interrogating transducer (B) and the forward scattered power is measured at a transducer (F) 180° removed from the interrogating transducer.

9. The method of claim 1, wherein, in step 3, the ultrasonic scattered power is measured at arbitrary angles.

10. The method of claim 1, wherein steps 1-3 are repeated one or more times at different concentrations of particles before step 4 is carried out, and wherein, in step 4, the scattered power measured at each concentration of particles is plotted to form a concentration curve and m is determined as the slope of the concentration curve.

11. The method of claim 7, wherein the value of K is first determined experimentally by carrying out the method of claim 11 using standard particles of known or estimated compressibility and density and calculating K according to the equation:

$$K = \frac{mr^2}{\left[\frac{\kappa_1 - \kappa_0}{\kappa_0} - \frac{3(\rho_1 - \rho_0)}{2\rho_1 + \rho_0}\right]^2 \left(\frac{1}{3}k_0^2 a^3\right)^2}.$$

12. The method of claim 7, wherein, in the computing step, the density of the particles is known and the compressibility of the particles is calculated according to the equation:

$$\frac{\kappa_1 - \kappa_0}{\kappa_0} = \frac{3(\rho_1 - \rho_0)}{2\rho_1 + \rho_0} + \frac{r\sqrt{\frac{m}{K}}}{\left(\frac{1}{3}k_0^2 a^3\right)}.$$

13. The method of claim 7, wherein it is known that the density term is very much smaller than the compressibility term and wherein the compressibility of the particles is calculated according to the equation:

$$\frac{\kappa_1 - \kappa_0}{\kappa_0} = \frac{r\sqrt{\frac{m}{K}}}{\left(\frac{1}{3}k_0^2 a^3\right)}.$$

14. The method of claim 8, wherein, in the computing step, the density contrast of the particles with the fluid medium is not known or, alternatively, is known not to be much smaller or larger than the compressibility contrast of the particles with the fluid medium, and wherein the compressibility of the particles is determined according to the equation:

$$\frac{\kappa_1 - \kappa_0}{\kappa_0} = \frac{r_B}{\frac{2}{3}(k_0^2 a^3)}\sqrt{\frac{m_B}{K}} + \frac{r_F}{\frac{2}{3}(k_0^2 a^3)}\sqrt{\frac{m_F}{K}},$$

where $m_B$ and $m_F$ are separate proportionality factors for backscattered (B) and forward scattered (F) power, respectively, and $r_B$ and $r_F$ are the distances from the transducer (B) and transducer (F), respectively, to the focal zone.

15. The method of claim 8, wherein, in the computing step, the compressibility contrast of the particles with the fluid medium is not known or, alternatively, is known not to be much smaller or larger than the density contrast of the particles with the fluid medium, and wherein the density of the particles is determined according to the equation:

$$\frac{3(\rho_1 - \rho_0)}{2\rho_1 + \rho_0} = \frac{r_F}{\frac{2}{3}(k_0^2 a^3)}\sqrt{\frac{m_F}{K}} - \frac{r_B}{\frac{2}{3}(k_0^2 a^3)}\sqrt{\frac{m_B}{K}},$$

where $m_B$ and $m_F$ are separate proportionality factors for backscatter (B) and forward scattering (F), respectively, and $r_B$ and $r_F$ are the distances from the transducer (B) and transducer (F), respectively, to the focal zone.

16. The method of claim 9, wherein, in the computing step, the density contrast of the particles with the fluid medium is not known or, alternatively, is known not to be much smaller or larger than the compressibility contrast of the particles with the fluid medium, wherein the backscattered power is measured at the interrogating transducer, wherein the second scattered power is measured at a transducer at an arbitrary angle θ removed from the interrogating transducer and wherein the compressibility of the particles is determined according to the equation:

$$\frac{\kappa_1 - \kappa_0}{\kappa_0} = \frac{3}{k_0^2 a^3 (1 + \cos\theta)}\left[r_\theta \sqrt{\frac{m_\theta}{K}} + \cos\theta r_B \sqrt{\frac{m_B}{K}}\right].$$

17. The method of claim 9, wherein, in the computing step, the compressibility contrast of the particles with the fluid medium is not known or, alternatively, is known not to be much smaller or larger than the density contrast of the particles with the fluid medium, wherein the backscattered power is measured at the interrogating transducer, wherein the forward scattered power is measured at a transducer at an arbitrary angle θ removed from the interrogating transducer and wherein the density of the particles is determined according to the equation:

$$\frac{(\rho_1 - \rho_0)}{2\rho_1 + \rho_0} = \frac{1}{k_0^2 a^3 (1 + \cos\theta)}\left[r_\theta \sqrt{\frac{m_\theta}{K}} - r_B \sqrt{\frac{m_B}{K}}\right].$$

18. A method for monitoring a change in small particle compressibility with pressure, the method comprising carrying out the following steps in the order given:
   (1) providing a fluid suspension comprising small particles to be tested and a compatible fluid medium;
   (2) placing the fluid suspension in a pressure vessel;
   (3) pressurizing the fluid suspension at a first pressure;
   (4) generating, from a transducer, an interrogating ultrasonic signal consisting of tone bursts of one or more frequencies directed into the fluid suspension, wherein the fluid suspension in the pressure vessel is in motion or is caused to become in motion by the interrogating signal;
   (5) measuring the ultrasonic scattered power from the interrogating signal;
   (6) determining a first proportionality factor m from the ratio of the scattered power to the concentration of the particles in the fluid medium;
   (7) computing a first compressibility from the proportionality factor m;
   (8) pressurizing the fluid suspension at a second pressure;
   (9) generating, from a transducer, an interrogating ultrasonic signal consisting of tone bursts of one or more frequencies directed into the fluid suspension, wherein the fluid suspension in the pressure vessel is in motion or is caused to become in motion by the interrogating signal;
   (10) measuring the ultrasonic scattered power from the interrogating signal;
   (11) determining a second proportionality factor m from the ratio of the scattered power to the concentration of the particles in the fluid medium;
   (12) computing a second compressibility from the second proportionality factor m; and
   (13) calculating any change in particle compressibility with the change in pressure.

19. A system for conducting both static and ultrasonic measurements of the compressibility of small particles, the system comprising:
- a pressure vessel for pressurizing a fluid suspension of particles contained within the vessel;
- apparatus for applying pressure to a fluid suspension contained in the vessel;
- a stirring mechanism for generating particle motion in a fluid suspension of particles;
- a transducer for generating an ultrasonic signal exposed to the inside of the vessel, whereby, when a fluid suspension of particles is contained within the vessel, the transducer is exposed to the fluid suspension; and
- one or more transducers for receiving scattered ultrasonic energy from the particles in a fluid suspension contained within the vessel.

20. The system of claim 19, wherein the transducer is directly exposable to the fluid suspension.

21. The system of claim 19, wherein the transducer is exposable to the fluid suspension through an ultrasonically transparent medium.

* * * * *

UNITED STATES PATENT AND TRADEMARK OFFICE
CERTIFICATE OF CORRECTION

| | | |
|---|---|---|
| PATENT NO. | : 7,844,405 B2 | |
| APPLICATION NO. | : 11/990472 | |
| DATED | : November 30, 2010 | |
| INVENTOR(S) | : Steven A. Africk | |

It is certified that error appears in the above-identified patent and that said Letters Patent is hereby corrected as shown below:

Column 7, line 4, "ofV" should read --of V--; and

Column 18, claim 11, line 64, "claim 11" should read --claim 7--.

Signed and Sealed this
Tenth Day of July, 2012

David J. Kappos
*Director of the United States Patent and Trademark Office*